(12) United States Patent
Lashure et al.

(10) Patent No.: US 12,053,189 B2
(45) Date of Patent: Aug. 6, 2024

(54) ORTHOPAEDIC BROACH EXTRACTION TOOL

(71) Applicant: DEPUY SYNTHES PRODUCTS, INC., Raynham, MA (US)

(72) Inventors: Daniel E. Lashure, Fort Wayne, IN (US); Cory A. Shulaw, Warsaw, IN (US)

(73) Assignee: DEPUY SYNTHES PRODUCTS, INC., Raynham, MA (US)

( * ) Notice: Subject to any disclaimer, the term of this patent is extended or adjusted under 35 U.S.C. 154(b) by 321 days.

(21) Appl. No.: 17/531,383

(22) Filed: Nov. 19, 2021

(65) Prior Publication Data

US 2022/0151641 A1 May 19, 2022

Related U.S. Application Data

(60) Provisional application No. 63/115,902, filed on Nov. 19, 2020.

(51) Int. Cl.
 *A61B 17/16* (2006.01)
(52) U.S. Cl.
 CPC ........ *A61B 17/1659* (2013.01); *A61B 17/164* (2013.01); *A61B 17/1668* (2013.01)
(58) Field of Classification Search
 CPC .............. A61B 17/1659; A61B 17/164; A61B 17/1668
 USPC ................................................ 606/79, 85, 99
 See application file for complete search history.

(56) References Cited

U.S. PATENT DOCUMENTS

| | | | |
|---|---|---|---|
| 4,715,860 A | 12/1987 | Amstutz et al. | |
| 4,795,473 A | 1/1989 | Grimes | |
| 5,002,580 A * | 3/1991 | Noble ................. | A61F 2/30724 623/23.23 |
| 5,037,424 A | 8/1991 | Aboczsky | |
| 5,089,003 A * | 2/1992 | Fallin ................. | A61B 17/1668 606/85 |
| 5,250,051 A | 10/1993 | Maryan | |
| 5,409,492 A * | 4/1995 | Jones ....................... | A61F 2/36 606/86 R |
| 5,683,399 A | 11/1997 | Jones | |
| 6,156,069 A | 12/2000 | Amstutz | |
| 6,322,564 B1 * | 11/2001 | Surma ................... | A61F 2/4607 606/89 |
| 7,879,042 B2 | 2/2011 | Long et al. | |
| 7,918,892 B2 | 4/2011 | Huebner | |
| 8,709,017 B2 | 4/2014 | Plassky et al. | |
| 10,646,354 B2 | 5/2020 | Huff et al. | |

(Continued)

FOREIGN PATENT DOCUMENTS

EP     684025 A1 *  11/1995  ......... A61B 17/1659
EP    1929964 A1    6/2008

(Continued)

*Primary Examiner* — Jessica Weiss
(74) *Attorney, Agent, or Firm* — Barnes & Thornburg LLP

(57) ABSTRACT

An apparatus, system, and method for extracting an orthopaedic broach from a bone of a patient comprises an orthopaedic broach extraction tool having a pair of jaws that are operable to secure the orthopaedic broach extraction tool to the orthopaedic broach. Once secured, the orthopaedic broach extraction tool can be used to facilitate extraction of the orthopaedic broach from the patient's bone using, for example, a reverse impaction tool.

18 Claims, 15 Drawing Sheets

(56) References Cited

U.S. PATENT DOCUMENTS

| | | | |
|---|---|---|---|
| 2005/0288676 A1* | 12/2005 | Schnieders | A61B 17/175 |
| | | | 606/79 |
| 2007/0162038 A1 | 7/2007 | Tuke | |
| 2007/0233136 A1 | 10/2007 | Wozencroft | |
| 2007/0299451 A1 | 12/2007 | Tulkis | |
| 2009/0209966 A1 | 8/2009 | Chandler | |
| 2010/0286700 A1 | 11/2010 | Snider et al. | |
| 2011/0004318 A1 | 1/2011 | Tulkis et al. | |
| 2012/0109225 A1* | 5/2012 | Krebs | A61F 2/461 |
| | | | 606/86 R |
| 2012/0290099 A1* | 11/2012 | Gibson | A61F 2/4637 |
| | | | 623/20.11 |
| 2015/0119648 A1* | 4/2015 | Barnett | A61B 17/2833 |
| | | | 600/226 |
| 2021/0212838 A1 | 7/2021 | Wright | |

FOREIGN PATENT DOCUMENTS

| | | | | |
|---|---|---|---|---|
| EP | 1961389 A1 | 8/2008 | | |
| WO | WO-2010006084 A2 * | 1/2010 | | A61F 2/4607 |

* cited by examiner

ORTHOPAEDIC BROACH EXTRACTION TOOL

CROSS-REFERENCE TO RELATED APPLICATIONS

This application claims priority under 35 U.S.C. § 119(e) to U.S. Provisional Patent Application No. 63/115,902, entitled "ORTHOPAEDIC BROACH EXTRACTION TOOL," which was filed on Nov. 19, 2020, which is incorporated by reference in its entirety.

TECHNICAL FIELD

The present disclosure relates generally to orthopaedic instruments for use in the performance of an orthopaedic joint replacement procedure, and more particularly to orthopaedic surgical instruments for extracting an orthopedic broach from a bone of a patient.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular prosthetic component and a femoral component prosthesis. An acetabular prosthetic component is implanted into the patient's acetabulum and generally includes an outer shell configured to engage the acetabulum and an inner bearing or liner coupled to the shell and configured to engage the femoral head. The femoral component prosthesis is implanted into the patient's femur and generally includes a stem component embedded into the medullary canal the femur and a femoral head prosthetic component. The femoral head prosthetic component and inner liner of the acetabular component form a ball and socket joint that approximates the natural hip joint.

To facilitate the replacement of the natural joint with a prosthetic hip joint or to replace an existing prosthetic hip joint, orthopaedic surgeons may use a variety of orthopaedic surgical instruments to prepare the patient's femur and/or acetabulum including, for example, broaches, reamers, drill guides, drills, positioners, and/or other surgical instruments. In some surgical techniques and/or under some circumstances, it may be necessary for the orthopaedic surgeon to remove orthopaedic surgical instruments from the patient's boney anatomy that have become lodged or "stuck" in place.

SUMMARY

According to an aspect of the present disclosure, an orthopaedic surgical instrument for extracting an orthopaedic broach from a bone of a patient includes a first body, a second body, and an adjustment screw. The first body includes a first main body and a first jaw extending distally from the first main body, and the first main body includes an aperture. The second body includes a second main body and a second jaw extending distally from the second main body, and the second main body includes a threaded aperture. The adjustment screw extends through the aperture of the first main body and is engaged into the threaded aperture of the second main body. Additionally, the adjustment screw is configured to be threaded into the threaded aperture of the second main body to cause the second jaw to move toward the first jaw or threaded out of the threaded aperture of the second main body to cause the second jaw to move away from the first jaw.

In some embodiments, the first jaw includes a first arm extending distally from a first end to a second end, with the first end of the first arm being attached to the first main body, and a first claw located at the second end of the first arm. Additionally, the second jaw may include a second arm extending distally from a first end to a second end, with the first end of the second arm being attached to the second main body, and a second claw located at the second end of the second arm, wherein the first claw and the second claw confront each other.

Additionally, in some embodiments, the first arm extends distally from the first main body at an angle toward the second arm and the second arm extends distally from the second main body at an angle toward the first arm such that a distance between the first end of the first arm and the first end of the second arm is greater than a distance between the second end of the first arm and the second end of the second arm.

In some embodiments, the threading of the adjustment screw into the threaded aperture of the second main body causes the second main body to translate along the adjustment screw toward the first main body. In such embodiments, the translation of the second main body toward the first main body decreases a distance between the first jaw and the second jaw. Additionally, in such embodiments, the first main body may include a track and the second main body may include a rail received in the track of the first main body. The rail may slide along the track when the second main body translates along the adjustment screw toward the first main body.

Additionally, in some embodiments, the adjustment screw may include an elongated screw body having a first end and a second end opposite the first end. The first end may include a threaded portion received in the threaded aperture of the second main body and a cap attached to a distal end of the threaded portion. The adjustment screw may also include a handle attached to the second end of the elongated screw body, and the handle may be operable to thread the elongated screw body into the threaded aperture of the second main body to cause the second main body to translate along the elongated screw body toward the first main body. In such embodiments, the elongated screw body may include a ring having a diameter greater than a diameter of the threaded portion and wherein the ring is captured in the first main body to secure the adjustment screw to the first main body.

In some embodiments, the first body may further include a threaded aperture located on a superior side of the first main body. For example, the first main body may include a boss extending superiorly from the superior side, and the boss may include the threaded aperture located on the superior side of the first main body.

According to another aspect, an orthopaedic surgical instrument system may include an orthopedic broach and an orthopaedic broach extraction tool. The orthopaedic broach may include a tapered body extending distally from a proximal end to a distal end, the tapered body having a plurality of cutting teeth defined therein. The orthopaedic broach extraction tool may include a first body, a second body, and an adjustment screw. The first body may include a first main body and a first jaw extending distally from the first main body, with the first main body including an aperture. The second body may include a second main body and a second jaw extending distally from the second main body. The second jaw may confront the first jaw and the second main body may include a threaded aperture. The adjustment screw may extend through the aperture of the first main body and be engaged into the threaded aperture of the second main body to couple the first body and the second body. The adjustment screw may be operable to cause the second jaw to move a first distance away from the first jaw that allows the orthopaedic broach to be positioned between the first jaw and the second jaw and may be operable to cause the second jaw to move toward the first jaw to cause the first jaw and the second jaw to engage the cutting teach of the orthopaedic broach while the orthopaedic broach is positioned between the first jaw and the second jaw to secure the orthopaedic broach extraction tool to the orthopaedic broach.

In some embodiments, the first jaw includes a first arm extending distally from a first end to a second end, with the first end of the first arm being attached to the first main body, and a first claw located at the second end of the first arm. Additionally, the second jaw may include a second arm extending distally from a first end to a second end, with the first end of the second arm being attached to the second main body, and a second claw located at the second end of the second arm, wherein the first claw and the second claw confront each other.

Additionally, in some embodiments, the first arm extends distally from the first main body at an angle toward the second arm and the second arm extends distally from the second main body at an angle toward the first arm such that a distance between the first end of the first arm and the first end of the second arm is greater than a distance between the second end of the first arm and the second end of the second arm.

In some embodiments, the threading of the adjustment screw into the threaded aperture of the second main body causes the second main body to translate along the adjustment screw toward the first main body. In such embodiments, the translation of the second main body toward the first main body decreases a distance between the first jaw and the second jaw. Additionally, in such embodiments, the first main body may include a track and the second main body may include a rail received in the track of the first main body. The rail may slide along the track when the second main body translates along the adjustment screw toward the first main body.

Additionally, in some embodiments, the adjustment screw may include an elongated screw body having a first end and a second end opposite the first end. The first end may include a threaded portion received in the threaded aperture of the second main body and a cap attached to a distal end of the threaded portion. The adjustment screw may also include a handle attached to the second end of the elongated screw body, and the handle may be operable to thread the elongated screw body into the threaded aperture of the second main body to cause the second main body to translate along the elongated screw body toward the first main body. In such embodiments, the elongated screw body may include a ring having a diameter greater than a diameter of the threaded portion and wherein the ring is captured in the first main body to secure the adjustment screw to the first main body.

In some embodiments, the first body may further include a threaded aperture located on a superior side of the first main body. For example, the first main body may include a boss extending superiorly from the superior side, and the boss may include the threaded aperture located on the superior side of the first main body.

According to a further aspect, a method of performing an orthopaedic surgical procedure on a proximal end of a patient's femur may include inserting an orthopaedic broach in a medullary canal of a patient's surgically prepared femur. The orthopaedic broach may include a tapered body extending distally from a proximal end to a distal end, the tapered body having a plurality of cutting teeth defined therein. The method may also include securing an orthopaedic broach extraction tool to the orthopaedic broach while the orthopaedic broach is inserted into the medullary canal of the patient's femur. Securing the orthopaedic broach extraction tool may include operating an adjustment screw of the orthopaedic broach extraction tool to move a second jaw of the orthopaedic broach extraction tool toward a first jaw of the orthopaedic broach extraction tool to cause the first and second jaws to engage the cutting teeth of the orthopaedic broach to secure the orthopaedic broach extraction tool to the orthopaedic broach. The method may further include extracting the orthopaedic broach from the medullary canal of the patient's femur using the orthopaedic broach extraction tool. The method may also include attaching a reverse impaction tool to the orthopaedic broach extraction tool and using the reverse impaction tool to extract the orthopaedic broach.

BRIEF DESCRIPTION OF THE DRAWINGS

The detailed description particularly refers to the following figures, in which.

Figure 12:
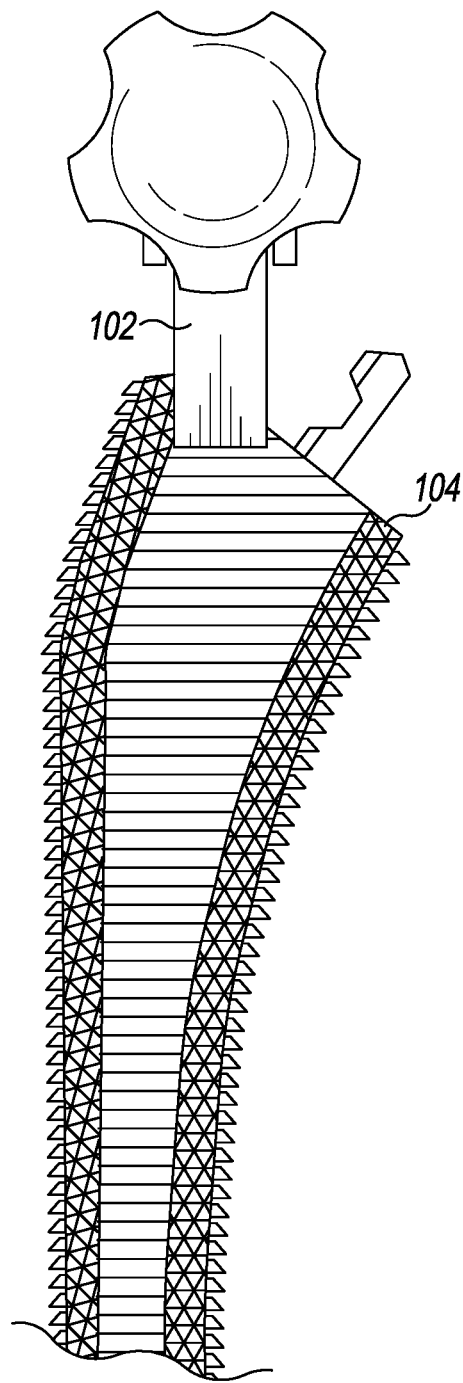
Figure 13:
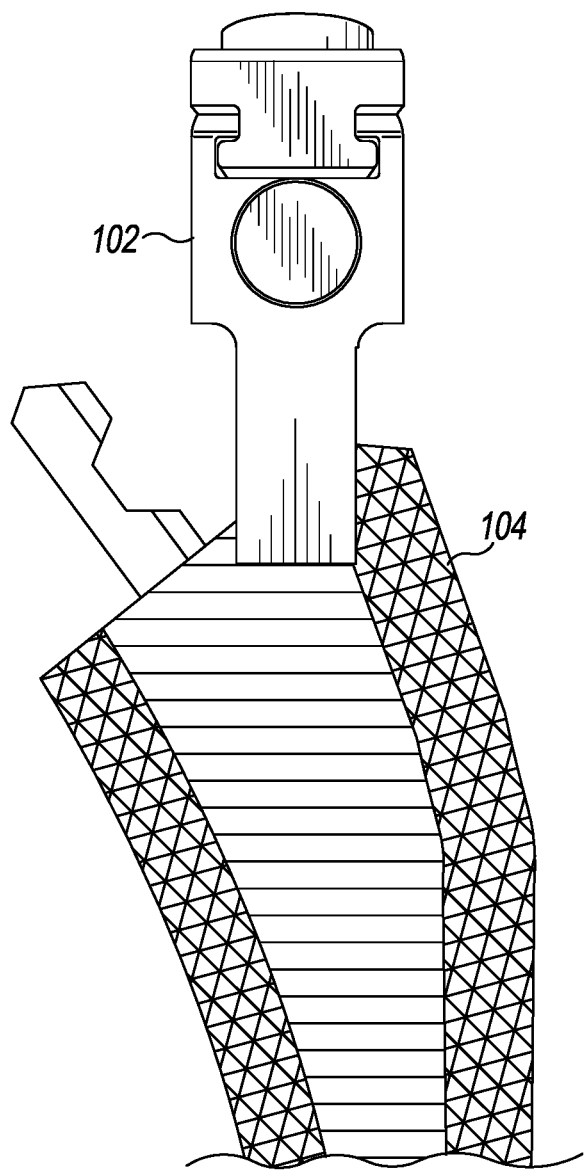
Figure 14:
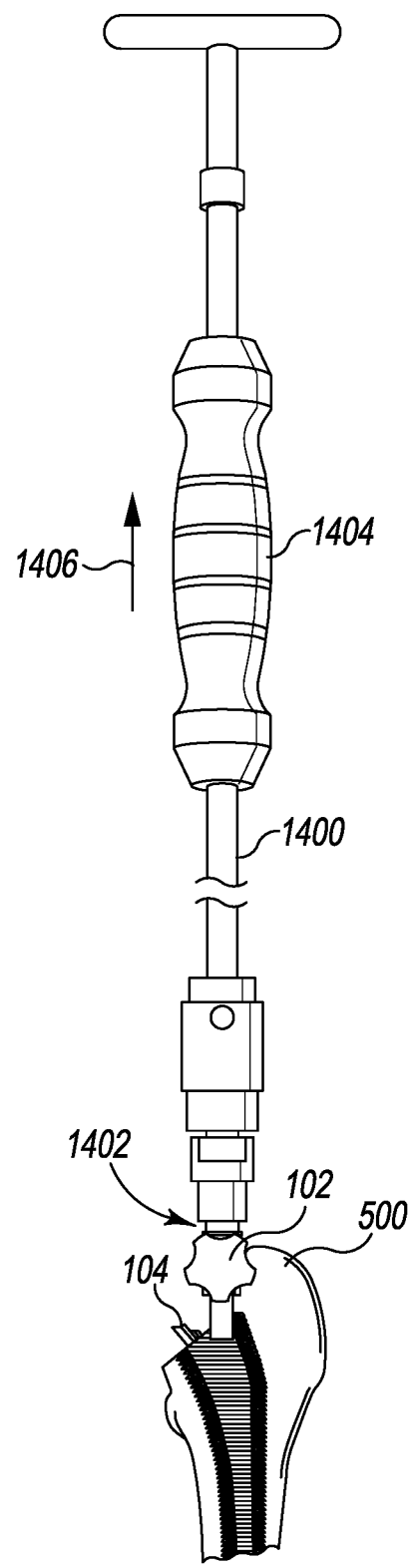
Figure 15:
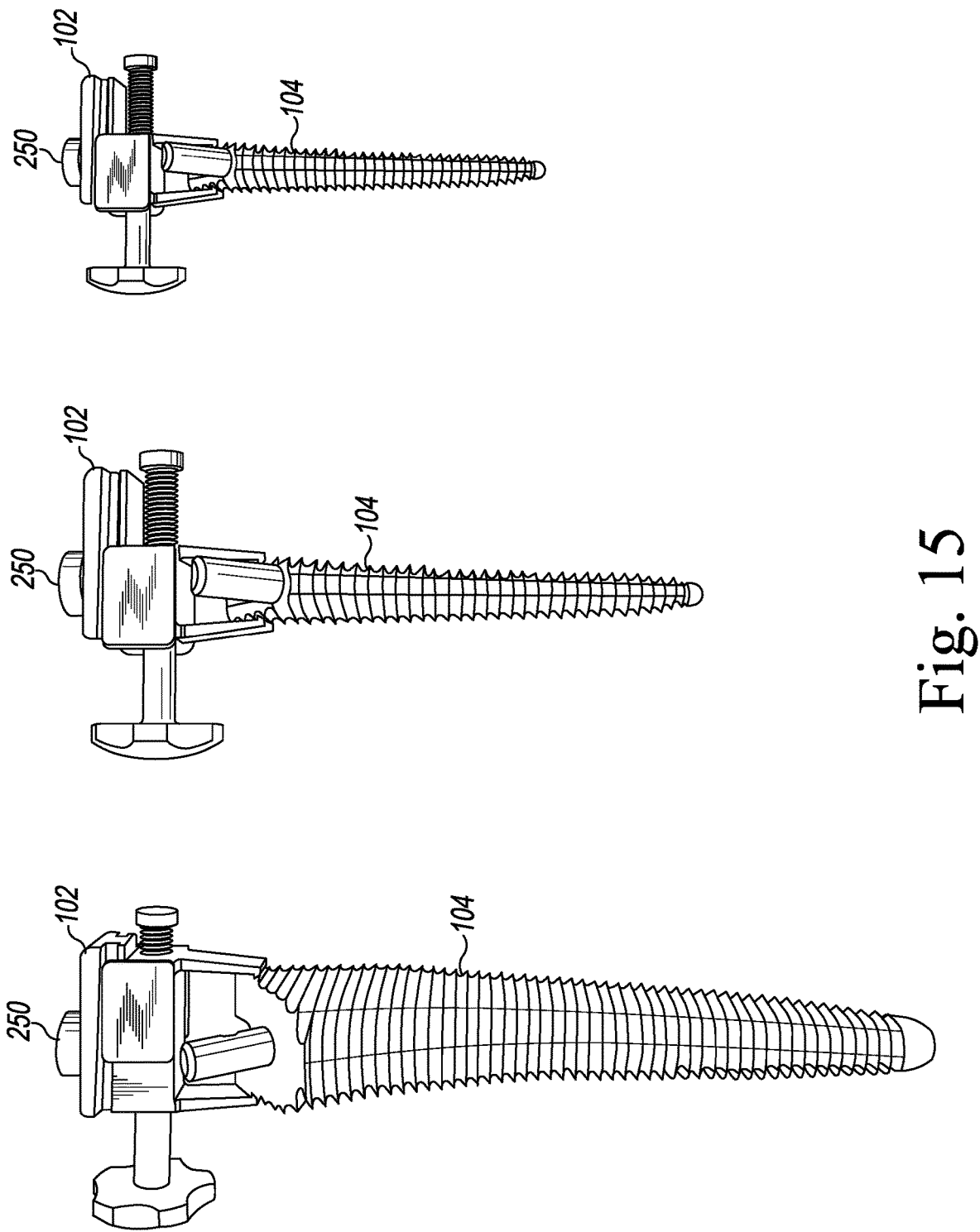

FIG. 12 is a posterior elevation view of the orthopaedic broach extraction tool and orthopaedic broach of FIG. 12 having the orthopaedic broach extraction tool secured to the orthopaedic broach;

FIG. 13 is an anterior elevation view of the orthopaedic broach extraction tool and orthopaedic broach of FIG. 12 having the orthopaedic broach extraction tool secured to the orthopaedic broach;

FIG. 14 is an anterior elevation of the orthopaedic broach extraction tool and orthopaedic broach of FIGS. 10-13 having a slap hammer secured to the orthopaedic broach extraction tool to assist in the removal of the orthopaedic broach from the patient's femur; and FIG. 15 is an elevation view of several different sizes of orthopaedic broach extraction tools and corresponding orthopaedic broaches.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise. While the disclosure below describes surgical instruments and techniques in reference to a patient's femur, it should be appreciated that all of the instruments and techniques described below may be used to surgically prepare other bones, such as, for example, a proximal end of a patient's tibia.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Figure 1:
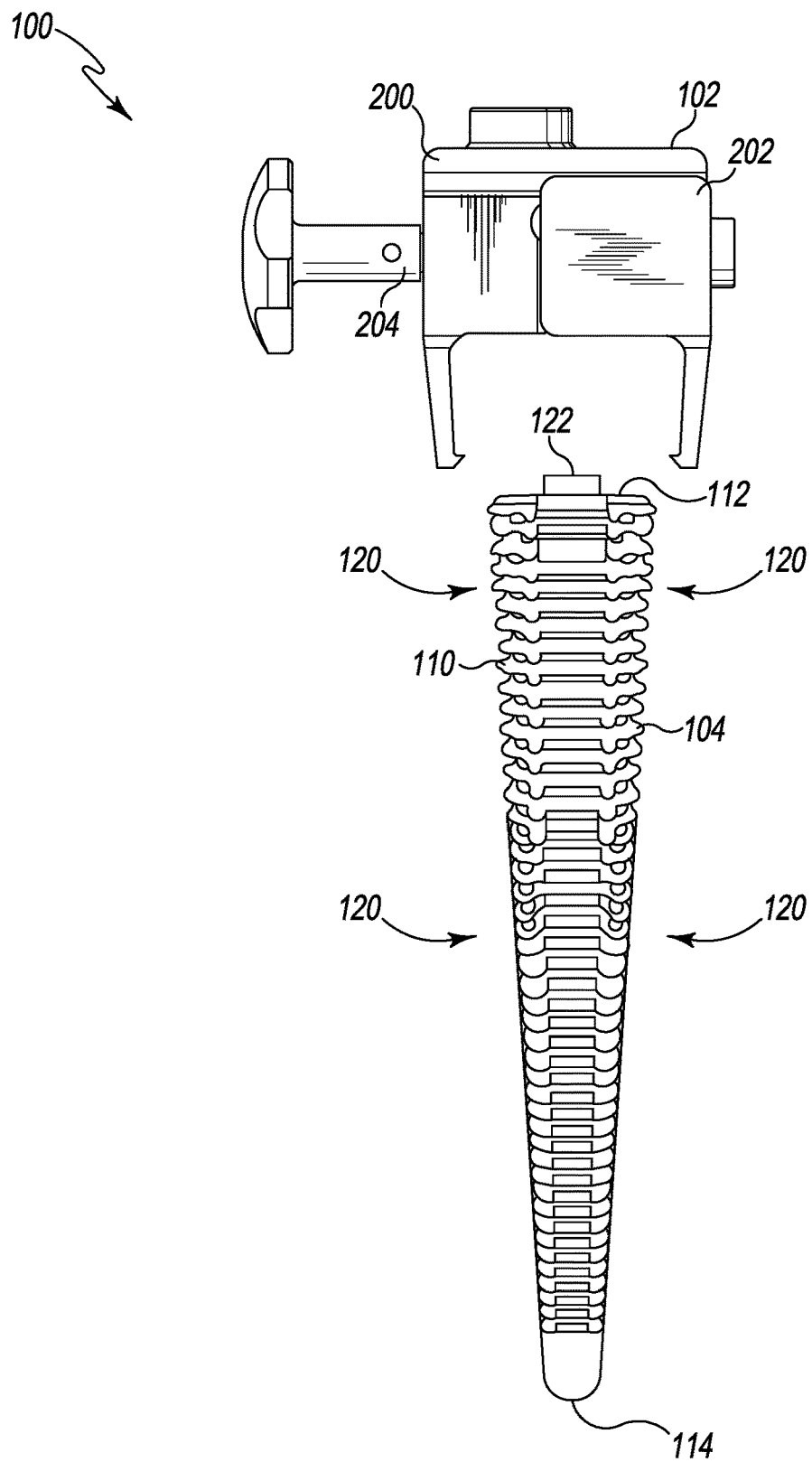
FIG. 1 is a side elevation view of an embodiment of an orthopaedic surgical instrument system including an orthopaedic broach and an orthopaedic broach extraction tool.
Figure 2:
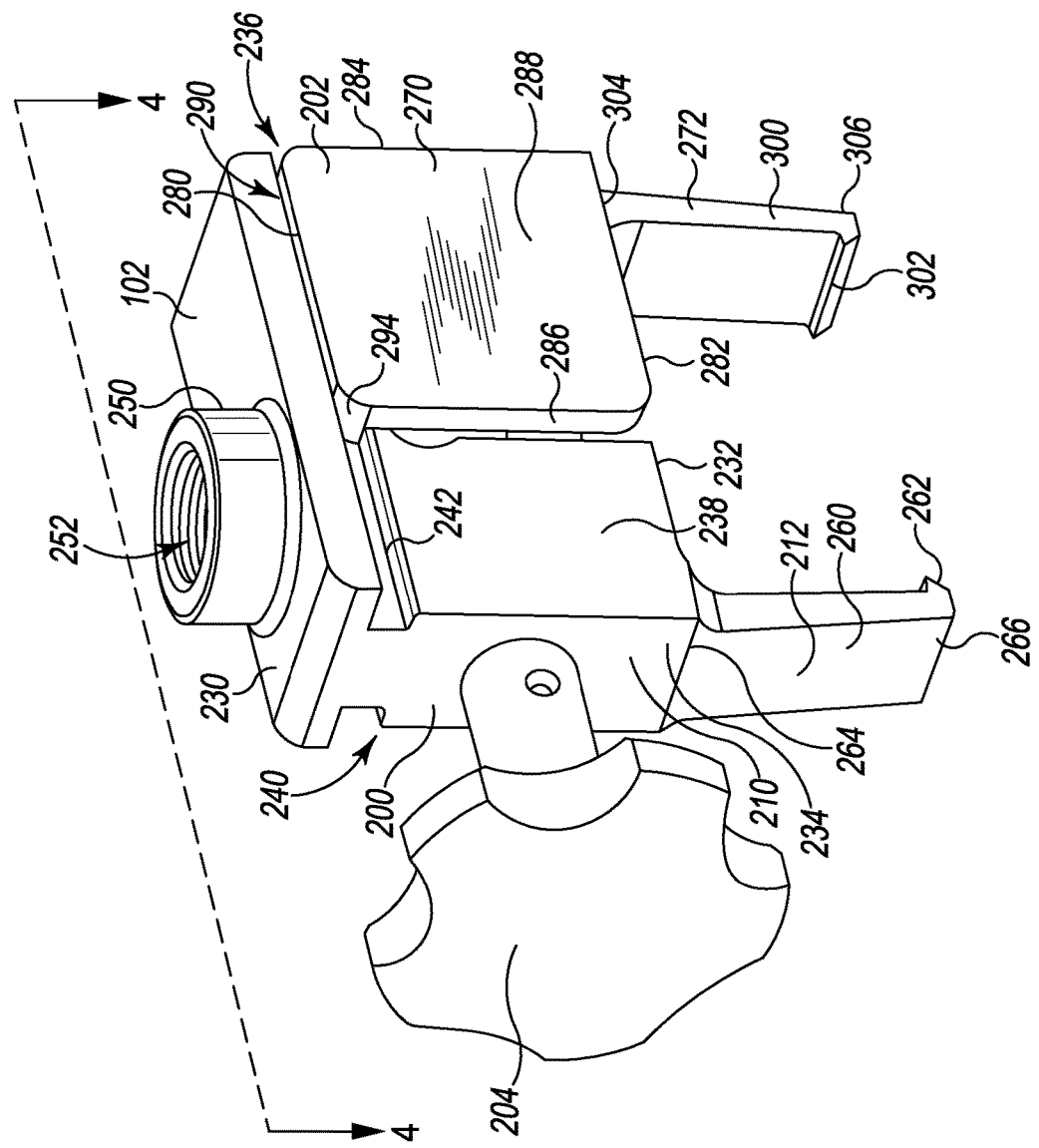
FIG. 2 is a perspective view of the orthopaedic broach extraction tool of the orthopaedic surgical instrument system of FIG. 1.

Referring now to FIG. 1, in an illustrative embodiment, an orthopaedic surgical instrument system 100 includes an orthopaedic broach extraction tool 102 and an orthopaedic broach 104. As discussed in more detail below, the orthopaedic broach extraction tool 102 is configured to facilitate the removal of the orthopaedic broach 104 from a bone of a patient (e.g., the patient's femur) in those situations in which removal of the broach is desirable.

Orthopaedic broaches are used during orthopaedic surgical procedures to prepare a corresponding bone of the patient. For example, an orthopedic broach may be used to widen a channel formed in the patient's bone (e.g., femoral bone) for receiving an orthopaedic implant. In some embodiments, the orthopaedic broach may be designed to remain in the patient's bone to form a foundation, or integral part of, the orthopaedic implant. However, in some situations or during some orthopaedic surgical procedures, it may be desirable to remove the orthopaedic broach from the patient's boney anatomy after implantation therein. In such cases, the design of the orthopaedic broach, the patient's boney anatomy, and other factors may create difficulties in removing the orthopaedic broach. As such, as discussed in more detail below, the orthopaedic broach extraction tool 102 may be used to improve the ease of removal of the orthopaedic broach 104 from the patient's boney anatomy.

The orthopaedic broach 104 is illustratively embodied as a femoral broach configured to be positioned in the medullary canal of the proximal end of the patient's femur. For example, the illustrative orthopaedic broach 104 is designed for use in a partial or total hip arthroplasty surgical procedure. Of course, in other embodiments, the orthopaedic broach 104 may be embodied as a different orthopaedic broach configured for use in the distal end of the patient's femur or on another bone of the patient.

The illustrative orthopaedic broach 104 is formed from a metallic material, such as 17-4 (630PH) Stainless Steel material, and includes an outer surface 110 extending from a proximal end 112 to a distal end 114. The outer surface 110 is tapered, with the diameter of the orthopaedic broach 104 decreasing from the proximal end 112 to the distal end 114.

A number of rows of cutting teeth 120 are formed on the outer surface 110 between the proximal end 112 and the distal end 114. The cutting teeth 120 are configured to engage the bone surrounding the medullary canal of the patient's femur when the orthopaedic broach 104 is inserted therein. It should be appreciated that multiple broaches 104 having different configurations may be provided in the orthopaedic surgical instrument system 100. For example, the outer diameter and/or length of each orthopaedic broach 104 may vary to produce different sized canals to accommodate prosthetic components of different sizes.

Figure 5:
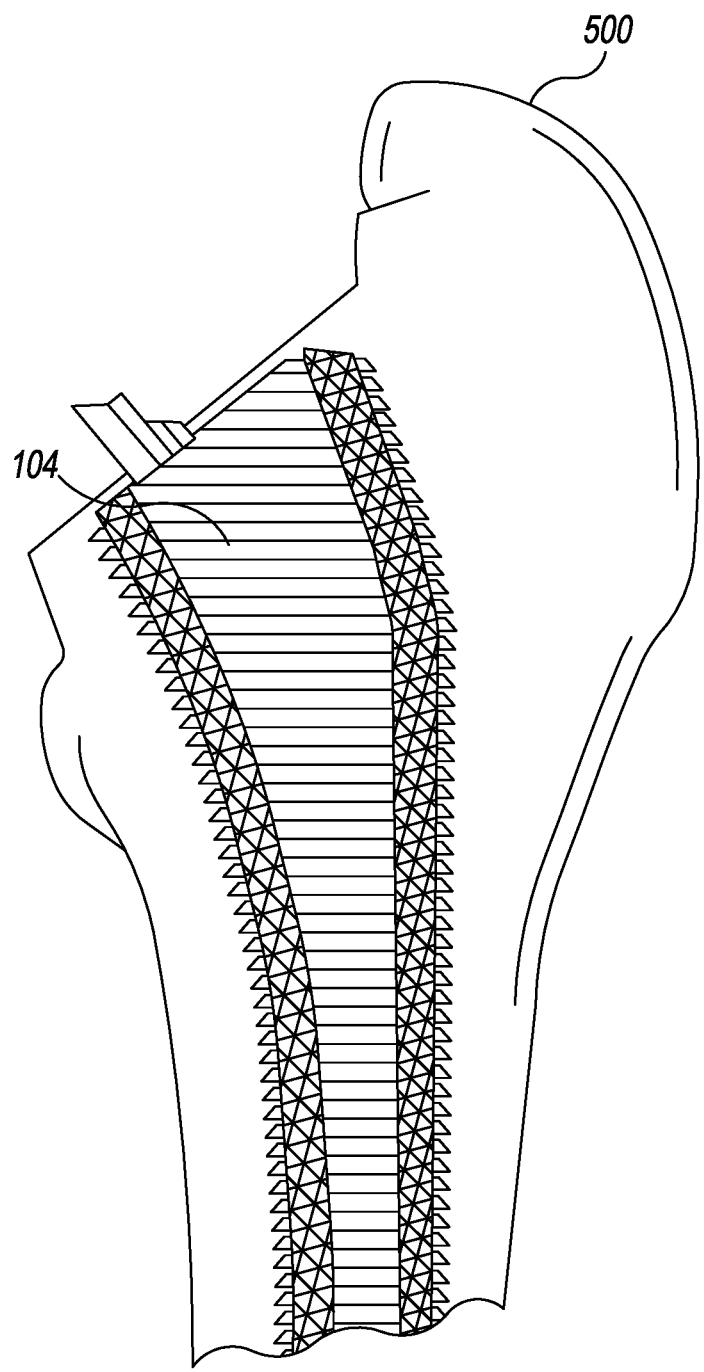
FIG. 5 is an anterior elevation view of a femur of a patient having a broach inserted therein.

The orthopaedic broach 104 is angled in the coronal plane to facilitate replacement of the femoral head and extension of the orthopaedic broach 104 into the medullary canal of the patient's femur (as best seen in FIG. 5). The orthopaedic broach 104 includes a boss 122 at the proximal end 112. In some embodiments, the boss 122 may form an attachment device to which orthopaedic prosthesis (e.g., a prosthetic femoral head) may be attached.

Referring now to FIGS. 1-4, the illustrative orthopaedic broach extraction tool 102 includes a stationary body 200, a movable body 202, and an adjustment screw 204 that couples the movable body 202 to the stationary body 200. As discussed in more detail below, the adjustment screw 204 is operable to cause the movable body 202 to move towards or away from the stationary body 200, which does not substantially move relative to the adjustment screw 204.

The orthopaedic broach extraction tool 102 is illustratively formed from a combination of a Custom 465 Stainless Steel material and a 17-4 (630PH) Stainless Steel material. For example, in the illustrative embodiment, the stationary body 200 is formed from a Custom 465 Stainless Steel material that has been heat treated using a H1000 heat treatment process and the movable body 202 and the adjustment screw 204 are formed from a 17-4 (630PH) Stainless Steel material heat treated using a H900 heat treatment process. Of course, the orthopaedic broach extraction tool 102 may be formed from other materials, such as a titanium material, in other embodiments.

The stationary body 200 includes a main body 210 and a jaw 212 extending distally from the main body 210. The main body 210 includes a superior side 230 and an inferior side 232 opposite the superior side 230. The main body 210 also includes a first lateral side 234, a second lateral side 236 opposite the first lateral side 234, a first elongated side 238, and a second elongated side 240 opposite the first elongated side 238. Each of the lateral sides 234, 236 and the elongated sides 238, 240 extend from the superior side 230 to the inferior side 232 to form an overall body having a substantially rectangular side profile.

The first elongated side 238 of the main body 210 includes a track 242 that extends from the first lateral side 234 to the second lateral side 236. As discussed in more detail below, the track 242 is configured to receive a rail 294 of the movable body 202 to guide the movable body 202 while the movable body 202 translates along the adjustment screw 204. The first elongated side 238 of the main body 210 also includes an inner wall 244 that defines a cavity 246 (see FIG. 4). The cavity 246 is sized to allow the movable body 202 to move therethrough as discussed further below.

Figure 4:
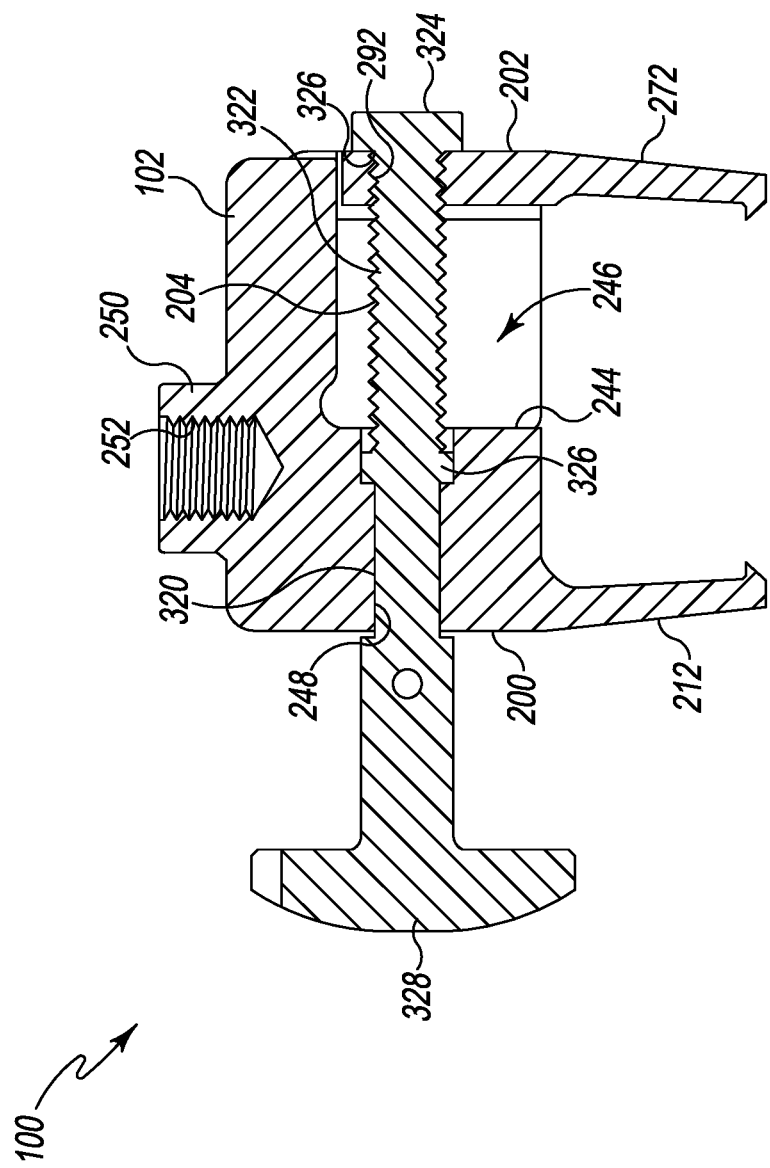
FIG. 4 is a cross-section view of the orthopaedic broach extraction tool of FIG. 2 taken generally along line 4-4 of FIG. 2.

The main body 210 also includes an aperture 248 through which the adjustment screw 204 is received (see FIG. 4). The aperture 248 is non-threaded and allows the adjustment screw 204 to freely rotate within the aperture 240. As shown best in FIG. 4, the adjustment screw 204 extends through the aperture 248 and into the cavity 246. As discussed in more detail below, the adjustment screw 204 is operable to cause the movable body 202 to translate along the adjustment screw 204. In doing so, the movable body 202 is moved through the cavity 246.

The main body 210 further includes a boss 250 located on the superior side 230. The boss 250 includes an internal threaded aperture 252 and, as discussed in more detail below, is configured to mate with a corresponding threaded end of a reverse impaction tool, such as a slap hammer, to facilitate the removal of the orthopaedic broach 104. Illustratively, the threaded aperture 252 includes a ⅜-16 thread, but may include an alternative thread pattern in other embodiments. Additionally, in some embodiments, the boss 250 is laterally located on the superior side 230 such that the boss 250 is coaxial with the orthopaedic broach 104 when the orthopaedic broach extraction tool 102 is secured to the orthopaedic broach 104. It should appreciated that such coaxial placement may improve the transfer of force generated by the reverse impaction tool to the orthopaedic broach 104 to further facilitate extraction thereof. Of course, the coaxial alignment of the boss 250 may depend on the relative size of the orthopaedic broach extraction tool 102 and the orthopaedic broach 104. For example, the orthopaedic broach extraction tool 102 may be designed for use on a size 5 orthopaedic broach 104, but may still be used on orthopaedic broaches 104 of other sizes. When so used, however, the boss 250 may be slightly off coaxial alignment with the different-sized broach 104.

The jaw 212 extends distally from the inferior side 232 of the main body 210. The jaw 212 includes an arm 260 and a claw 262. The arm 260 includes a proximal end 264 attached to the inferior side 232 of the main body 210 and a distal end 266. The claw 262 is located at the distal end 266 of arm 260 and faces toward the movable body 202.

The movable body 202 also includes a main body 270 and a jaw 272 extending distally from the main body 270. Similar to the main body 210 of the stationary body 200, the main body 270 of the movable body 202 includes a superior side 280 and an inferior side 282 opposite the superior side 280. The main body 270 also includes a first lateral side 284, a second lateral side 286 opposite the first lateral side 284, a first elongated side 288, and a second elongated side 290 opposite the first elongated side 288. Each of the lateral sides 284, 286 and the elongated sides 288, 290 extend from the superior side 280 to the inferior side 282 to form an overall body having a substantially rectangular side profile.

The main body 270 includes a threaded aperture 292 through which a second threaded end 322 of the adjustment screw 204 is received. In this way, the adjustment screw 204 couples the movable body 202 to the stationary body 204. Additionally, the main body 270 includes a rail 294 extending from the elongated side 290. The rail 294 extends from the first lateral side 284 to the second lateral side 286 of the main body 270. As discussed above, the rail 292 is received in the track 242 of the main body 210 of the stationary body 200 to guide the movable body 270 while it translates along the adjustment screw 204. That is, as discussed in more detail below, the adjustment screw 204 is operable to be threaded into and out of the threaded aperture 292. As the adjustment screw 204 is threaded through the threaded aperture 292, the movable body 202 translates along the adjustment screw 206 and into the cavity 246 of the stationary body 200. In doing so, the rail 292 of the main body 270 slides along the track 242 of the main body 210 to provide stability to the movable body 202. Conversely, as the adjustment screw 204 is unthreaded from the threaded aperture 292, the movable body 202 translates along the adjustment screw 206 through the cavity 246 the stationary body 200 and the rail 292 of the main body 270 slides along the track 242 of the main body 210 to provide stability to the movable body 202.

Figure 3:
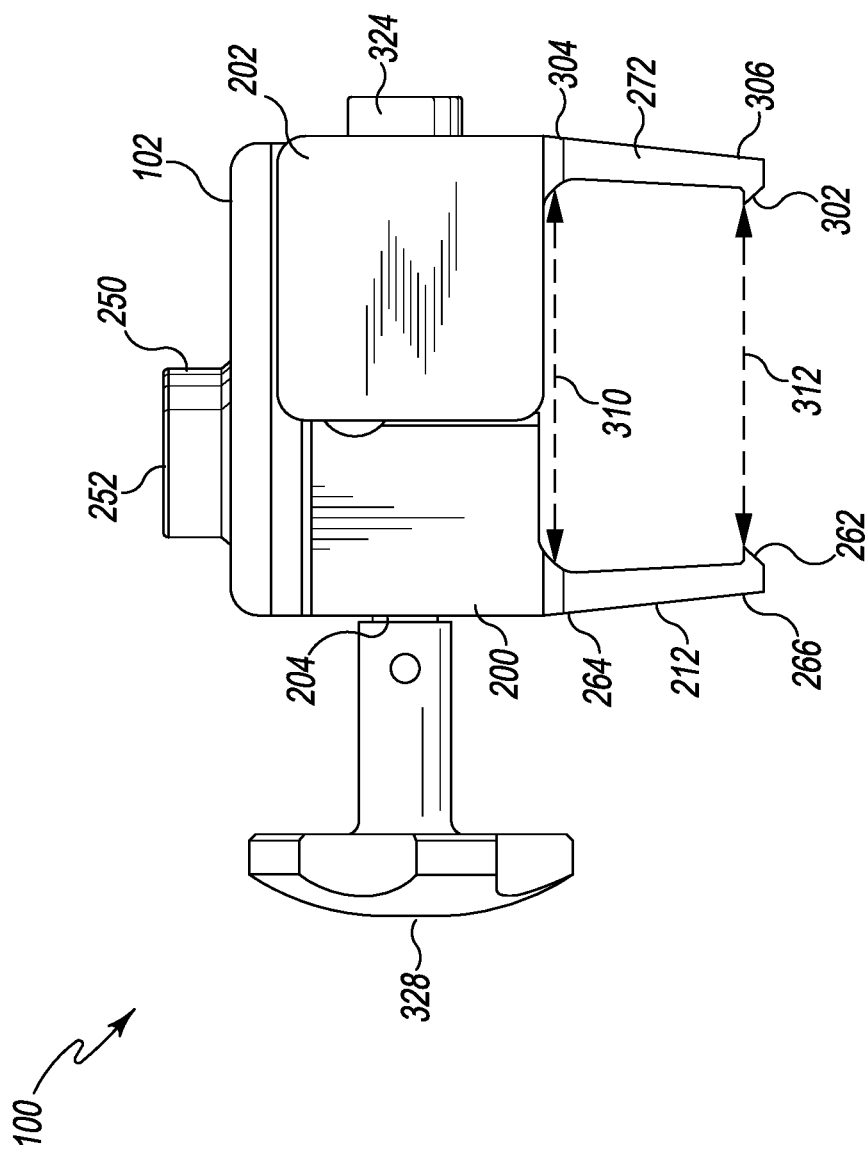
FIG. 3 is a side elevation view of the orthopaedic broach extraction tool of FIG. 2.

The jaw 272 extends distally from the inferior side 282 of the main body 270. Similar to the jaw 212 of the stationary body 200, the jaw 212 includes an arm 300 and a claw 302. The arm 300 includes a proximal end 304 attached to the inferior side 282 of the main body 270 and a distal end 306. The claw 302 is located at the distal end 306 of arm 300 and faces toward the stationary body 200. As best shown in FIG. 3, each of the jaws 212, 272 extend respectively from the inferior sides 232, 282 at an angle relative to the corresponding inferior sides 232, 282. In particular, the jaws 212, 272 extend at an angle toward each other such that a distance 310 between the proximal ends 264, 304 of the jaws 212, 272 is greater than a distance 312 between the distal ends 266, 306 of the jaws 212, 272. Additionally, it should be appreciated that although each of the jaws 212, 272 are shown and described as including a single claw 262, 302, each jaw may include multiple claws in other embodiments.

The adjustment screw 204 includes an elongated screw body having a first end 320 and the second threaded end 322 opposite the first end 320. The second threaded end 322 is received in the threaded aperture 292 of the movable body 202. The second threaded end 322 includes a cap 324 secured to a distal end 326. The cap 324 may be attached to the second threaded end 322 via press fitting, welding, and/or other securement mechanism. Regardless, it should be appreciated that the cap 324 has a diameter greater than the second threaded end 322 to restrict the adjustment screw 204 from unthreading completely from the threaded aperture 292.

The second threaded end 322 extends from the threaded aperture 292 of the movable body 202, through the cavity 246 of the stationary body 200, to the first end 320, which is received in the aperture 248. As discussed above, the aperture 248 is non-threaded to allow the adjustment screw 204 to freely rotate therein. The first end 320 of the adjustment screw 204 includes a ring stop 326. The ring stop 326 has a diameter greater the diameter of the aperture 248 to restrict lateral movement of the adjustment screw 204 through the aperture 248.

The adjustment screw 204 includes a knob 328 attached to a distal end 330 of the first end 320. The knob 328 is illustratively embodied as a scalloped knob, but other handles/knobs may be used in other embodiments. For example, the knob 328 may be embodied as a T-handle, a nut driver, an internal/external socket, or other fixture capable of operation to thread the second threaded end into/out of the threaded aperture 248 of the movable body 202.

In use, as discussed in more detail below, the adjustment screw 204 is operable to move the jaws 212, 272 toward and away from each other. To do so, an orthopaedic surgeon may turn the knob 328 to cause the second threaded end 322 to thread through or out of the threaded aperture 292 of the movable body 202. The threading of the second threaded end 322 through the threaded aperture 292 causes the movable body 202 to translate along the adjustment screw 204 toward the stationary body 200, which causes the jaw 272 to move toward the jaw 212. Conversely, the unthreading of the second threaded end 322 from the threaded aperture 292 causes the movable body 202 to translate along the adjustment screw 204 away from the stationary body 200, which causes the jaw 272 to move away the jaw 212.

While a particular embodiment of the orthopaedic broach extraction tool 102 has been shown in FIGS. 1-4 and described above, it should be appreciated that the orthopaedic broach extraction tool 102 may have alternative or additional features in other embodiments. For example, in some embodiments, the adjustment screw 204 may be replaced with a spring mechanism that biases the jaws 212, 272 toward each other. In such embodiments, the orthopaedic broach extraction tool 102 may be attached to an orthopaedic broach 104 by temporarily overcoming the biasing force of the spring mechanism to expand the jaws 212, 272 away from each other to allow the orthopaedic broach 104 to be received therebetween. Additionally, in some embodiments, the stationary body 200 and the movable body 202 may be swapped in position. Additionally, in other embodiments, the jaws 212, 272 may be embodied as tilt jaws that close and open toward each other via a top-side threaded screw similar to a pulley puller. Furthermore, in some embodiments, the orthopaedic broach extraction tool 102 may be integrated with the reverse impaction tool to form a singular or monolith orthopaedic surgical tool.

Referring now to FIGS. 5-14, the orthopaedic broach extraction tool 102 may be used during the performance of an orthopaedic surgical procedure to extract the orthopaedic broach 104 from a femur 500 of a patient. As shown in FIG. 5, the orthopaedic broach 104 may be implanted into the femur 500 of the patient during a stage of the orthopaedic surgical procedure. For various reasons, however, it may be desirable to subsequently remove the orthopaedic broach 104 from the patient's femur 500. To do so, the orthopaedic surgeon may use the orthopaedic broach extraction tool 102.

Figure 6:
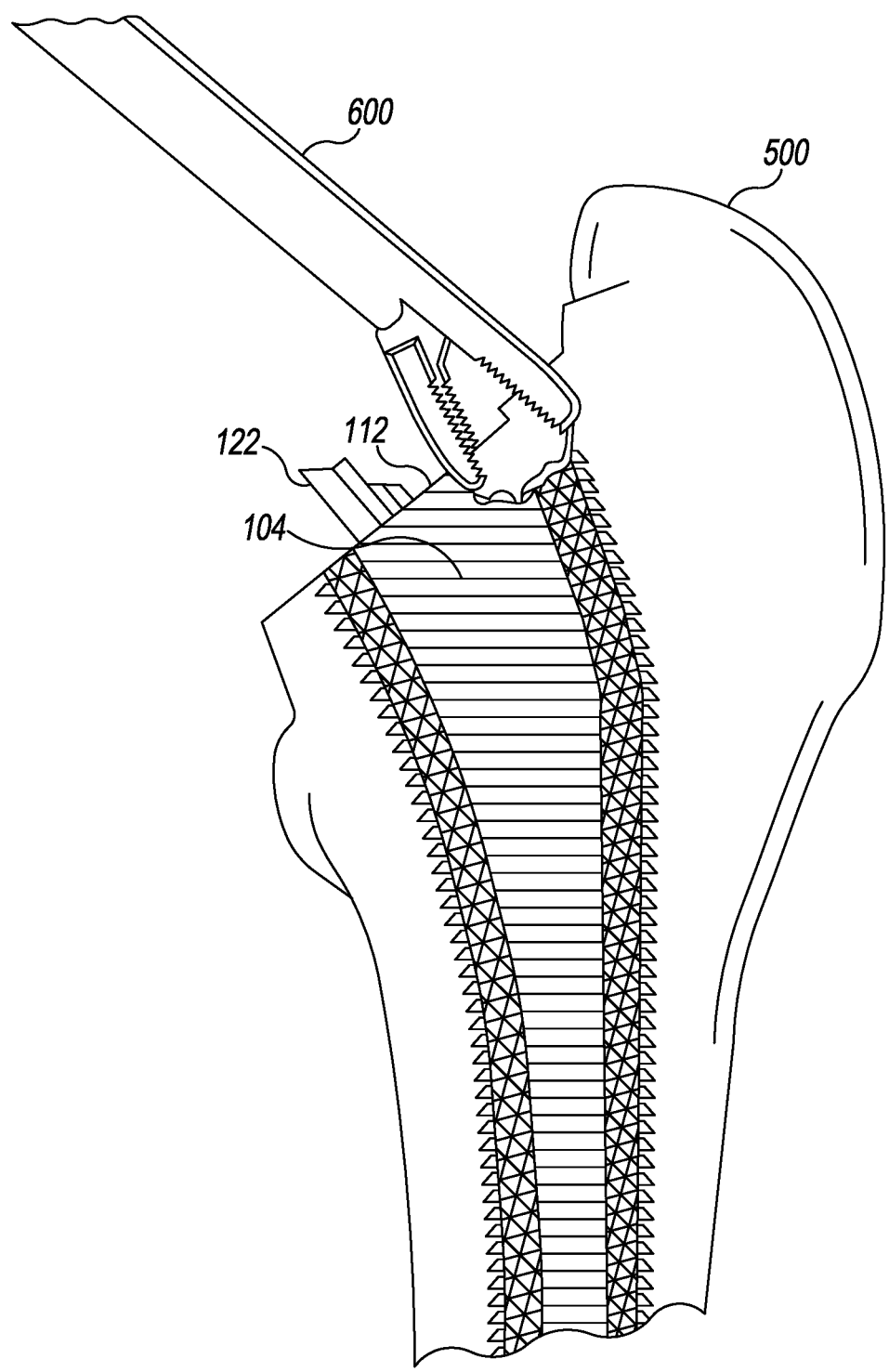
FIG. 6 is an anterior elevation view of the patient's femur of FIG. 5 having a portion of the bone removed to expose anterior and posterior portions of the superior end of the orthopaedic broach.

As shown in FIG. 6, the patient's femur 500 is further surgically prepared to allow use of the orthopaedic broach extraction tool 102. To do so, the orthopaedic surgeon removes a portion of the anterior and posterior bone of the proximal end of the patient's femur 500 that is medial of the greater trochanter. The removed portions of the patient's femur exposes the lateral portion of the superior end 112 of the orthopaedic broach 104 and provide room for the jaws 212, 272 of the orthopaedic broach extraction tool 102 to engage the superior teeth of the orthopaedic broach 104. The anterior and posterior portions of the patient's femur 500 may be removed using a bone saw, a bone rongeur, or other orthopaedic bone-removal tool 600. In some embodiments, only bone sufficient enough to expose the first one or two rows of teeth of the orthopaedic broach 104 need be removed from the patient's femur 500.

Figure 7:
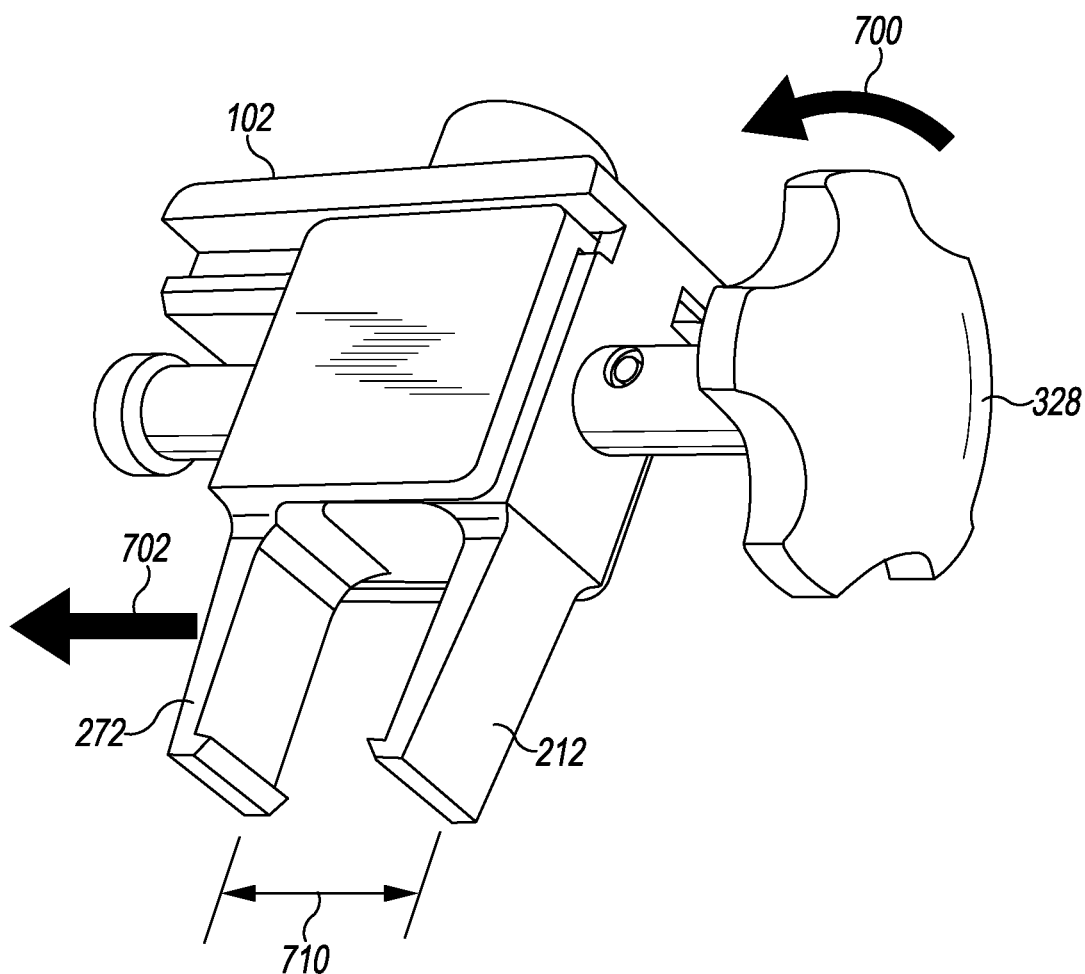
FIG. 7 is a perspective view of the orthopaedic broach extraction tool of the orthopaedic surgical instrument system of FIG. 1 showing a pair of jaws of the orthopaedic broach extraction tool in the process of being opened by operation of an adjustment screw of the orthopaedic broach extraction tool.

The orthopaedic broach extraction tool 102 may then be prepared to be secured to the exposed portion of the orthopaedic broach 104. To do so, as shown in FIG. 7, the orthopaedic surgeon may operate the knob 328 of the adjustment screw 204 to cause the jaw 272 to move away from the jaw 212. For example, the orthopaedic surgeon may rotate the knob 328 in a counter-clockwise direction 700 (depending on thread direction of the second threaded end 322) to cause the jaw 272 to translate in a direction 702 away from the jaw 212. In so doing, a distance 710 defined between the jaws 212, 272 is increased to a sufficient size to allow the superior end of the orthopaedic broach 104 to be received between the jaws 212, 272.

Figure 8:
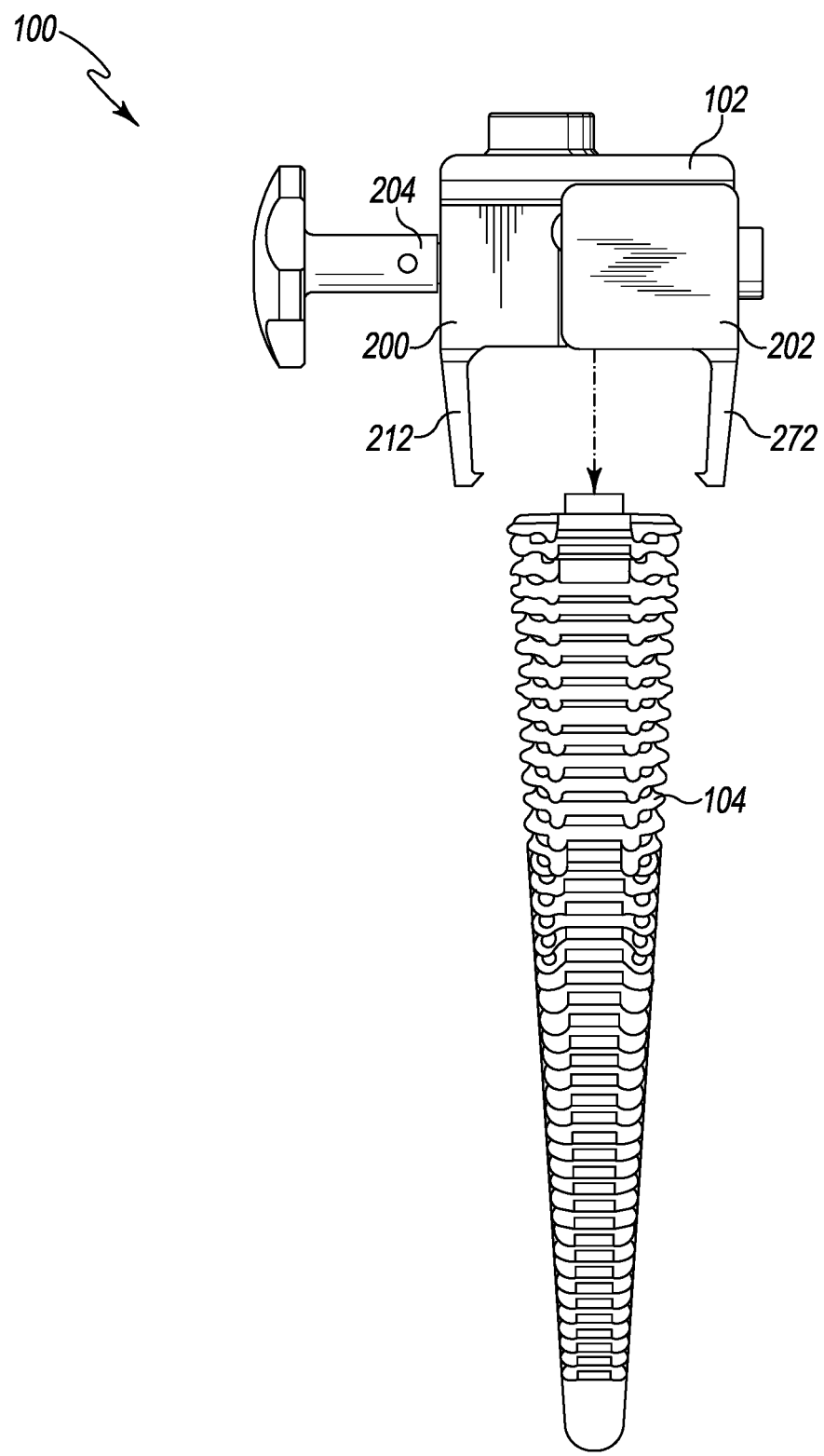
FIG. 8 is a side elevation view of the orthopaedic broach extraction tool of FIG. 7 having the pair of jaws in the opened position and in the process of being secured to the orthopaedic broach, and with the patient's femur not shown for clarity.
Figure 9:
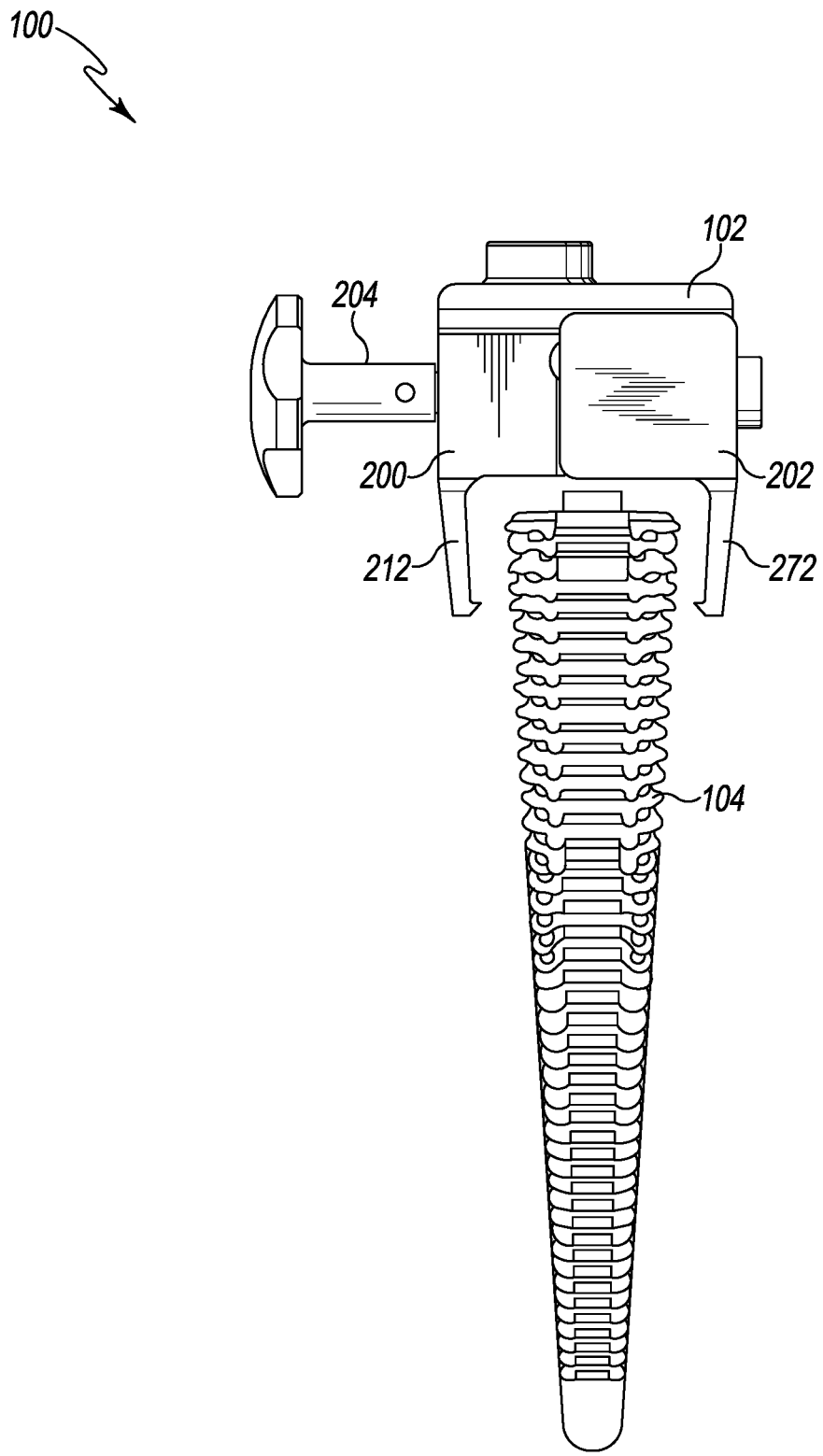
FIG. 9 is a side elevation view of the orthopaedic broach extraction tool of FIG. 8 having the orthopaedic broach received between the opened pair of jaws of the orthopaedic broach extraction tool, and with the patient's femur not shown for clarity.

After the jaws 212, 272 have been extended a sufficient distance 710 from each other, the orthopaedic broach extraction tool 102 is positioned over the superior end of the orthopaedic broach 104 as shown in FIGS. 8 and 9. In particular, the orthopaedic broach extraction tool 102 is positioned over the orthopaedic broach 104 such that the jaws 212, 272 are capable of contacting the superior lateral end of the orthopaedic broach 104, which was previously exposed by the orthopedic surgeon as discussed above in regard to FIG. 6.

Figure 10:
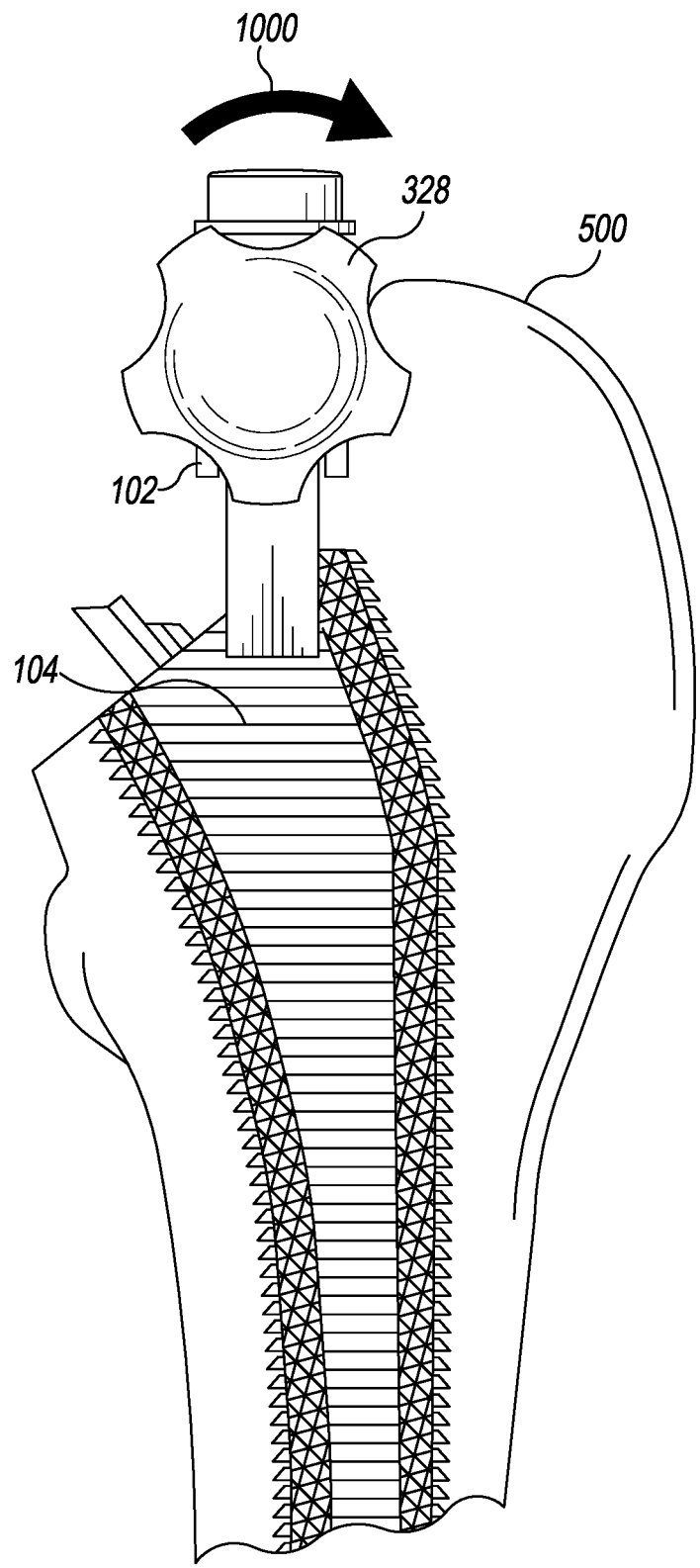
FIG. 10 is anterior elevation view of the orthopaedic broach extraction tool and orthopaedic broach of FIG. 9 showing operation of the adjustment screw of the orthopaedic broach extraction tool to secure the orthopaedic broach extraction tool to the orthopaedic broach.
Figure 11:
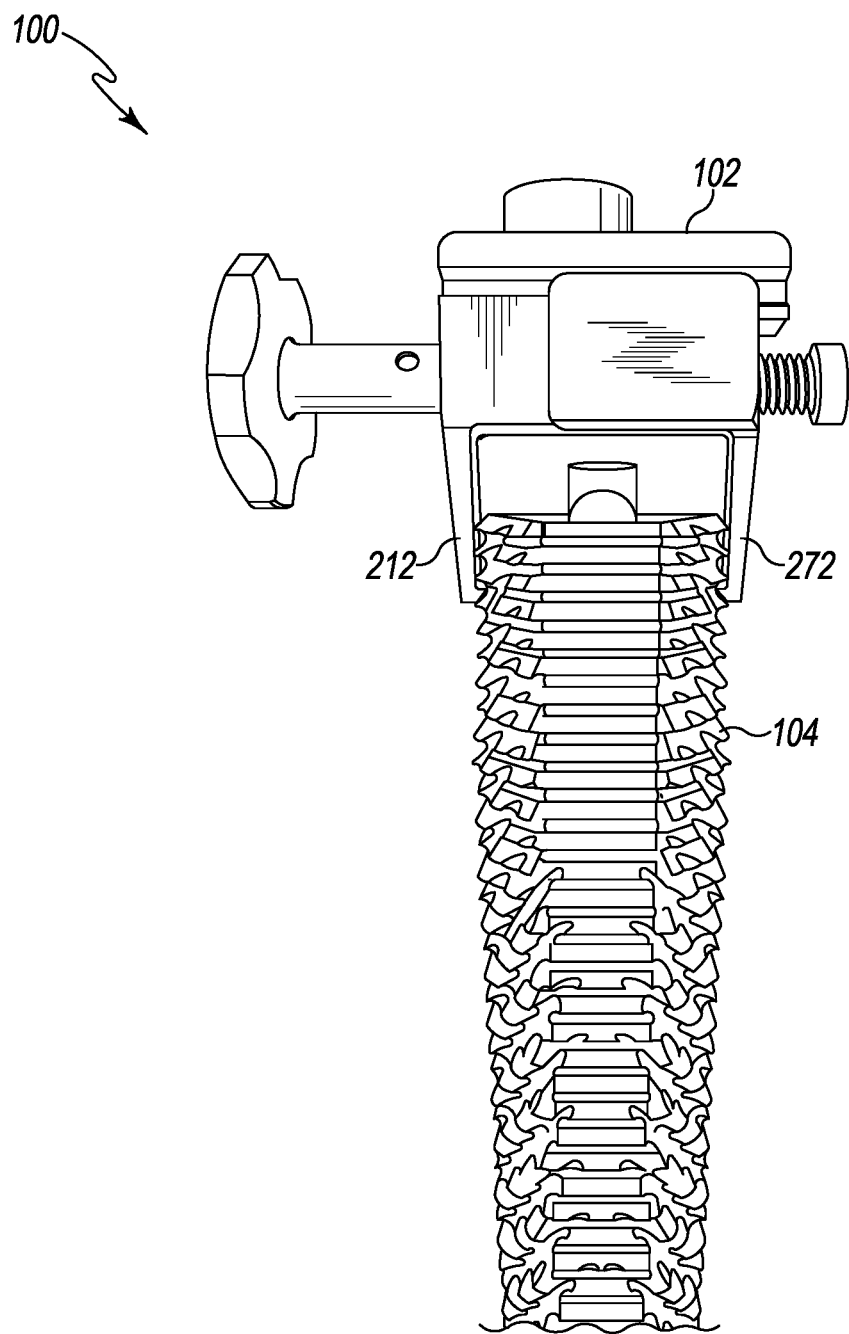
FIG. 11 is a lateral side elevation view of the orthopaedic broach extraction tool and orthopaedic broach of FIG. 10 after operation of the adjustment screw to cause the pair of jaws of the orthopaedic broach extraction tool to engage teeth of the orthopaedic broach to secure the orthopaedic broach extraction tool to the orthopaedic broach, and with the patient's femur not shown for clarity.

After the orthopaedic broach extraction tool 102 has been properly positioned over the superior end of the orthopaedic broach 104, the orthopaedic surgeon may operate the knob 328 of the adjustment screw 204 to cause the jaw 272 to move toward from the jaw 212 to secure the orthopaedic broach extraction tool 102 to the orthopaedic broach 104. For example, as shown in FIG. 10, the orthopaedic surgeon may rotate the knob 328 in a clockwise direction 1000 (depending on thread direction of the second threaded end 322) to cause the jaw 272 to translate toward from the jaw 212. In so doing, the claws 262, 302 of the jaws 212, 272 engage and mate with the teeth 120 of the orthopaedic broach 104 as best shown in FIGS. 11-13 (with the patient's femur 500 not shown for clarity). In the illustrative embodiment, the claws 262, 302 of the jaws 212, 272 are configured to engage one of the first few teeth 120 of the superior end of the orthopaedic broach 104. In this way, the amount of femoral bone that is required to be removed to allow securement of the orthopaedic broach extraction tool 102 to the orthopaedic broach 104 is reduced.

Referring now to FIG. 14, after the orthopaedic broach extraction tool 102 has been properly secured to the orthopaedic broach 104 via interaction of the claws 262, 302 and the teeth 120, the orthopaedic surgeon may attach a reverse impaction tool 1400 (e.g., a "slap hammer") to the orthopaedic broach extraction tool 102. To do so, the orthopaedic surgeon may thread a threaded end 1402 of the reverse impaction tool 1400 into the threaded aperture 252 of the boss 250 located on the superior side 230 of the stationary body 200. Once so attached, the orthopaedic surgeon may operate the reverse impaction tool 1400 to extract the orthopaedic broach 104 from the patient's femur 500. For example, the orthopaedic surgeon may repeatedly slide a weighted handle 1404 of the reverse impaction tool 1400 in a direction 1406 away from the orthopaedic broach extraction tool 102 to transfer an upward force to the orthopaedic broach 104.

Referring now to FIG. 15, it should be appreciated that the orthopaedic broach extraction tool 102 may be provided in different sizes configured to be used with corresponding sizes of orthopaedic broaches 104. As discussed above, by matching an appropriately sized orthopaedic broach extraction tool 102 with a correspondingly sized orthopaedic broach 104, the boss 250 of the orthopaedic broach extraction tool 102 (and thereby the reverse impaction tool) may be better coaxially aligned with the orthopaedic broach 104. Such coaxial alignment between the orthopaedic broach extraction tool 102 and the corresponding orthopaedic broach 104 may improve force transverse between the reverse impaction tool and the orthopaedic broach 104. Of course, a orthopaedic broach extraction tool 102 may be used with varying sizes of orthopaedic broaches 104 (e.g., a defined range of sizes) in other embodiments.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

The invention claimed is:

1. An orthopaedic surgical instrument for extracting an orthopaedic broach from a bone of a patient, the orthopaedic surgical instrument comprising:
   a first body having a first main body and a first jaw extending distally from the first main body, wherein the first main body includes an aperture and a track;
   a second body having a second main body and a second jaw extending distally from the second main body, wherein the second main body includes a threaded aperture and a rail received in the track of the first main body; and
   an adjustment screw extending through the aperture of the first main body and engaged into the threaded aperture of the second main body, wherein the adjustment screw is configured to be threaded into the threaded aperture of the second main body to cause the second jaw to move toward the first jaw, and wherein the rail slides along the track when the second jaw is moved toward the first jaw.

2. The orthopaedic surgical instrument of claim 1, wherein the first jaw comprises (i) a first arm extending distally from a first end to a second end, wherein the first end of the first arm is attached to the first main body, and (ii) a first claw located at the second end of the first arm, and
   wherein the second jaw comprises (ii) a second arm extending distally from a first end to a second end, wherein the first end of the second arm is attached to the second main body, and (ii) a second claw located at the second end of the second arm, wherein the first claw and the second claw confront each other.

3. The orthopaedic surgical instrument of claim 2, wherein the first arm extends distally from the first main body at an angle toward the second arm and wherein the second arm extends distally from the second main body at an angle toward the first arm such that a distance between the first end of the first arm and the first end of the second arm is greater than a distance between the second end of the first arm and the second end of the second arm.

4. The orthopaedic surgical instrument of claim 1, wherein the threading of the adjustment screw into the threaded aperture of the second main body causes the second main body to translate along the adjustment screw toward the first main body.

5. The orthopaedic surgical instrument of claim 4, wherein translation of the second main body toward the first main body decreases a distance between the first jaw and the second jaw.

6. The orthopaedic surgical instrument of claim 1, wherein the adjustment screw comprises (i) an elongated screw body having a first end and a second end opposite the first end, wherein the first end includes a threaded portion received in the threaded aperture of the second main body and a cap attached to a distal end of the threaded portion and (ii) a handle attached to the second end of the elongated screw body, wherein the handle is operable to thread the elongated screw body into the threaded aperture of the second main body to cause the second main body to translate along the elongated screw body toward the first main body.

7. The orthopaedic surgical instrument of claim 6, wherein the elongated screw body further includes a ring having a diameter greater than a diameter of the threaded portion and wherein the ring is captured in the first main body to secure the adjustment screw to the first main body.

8. The orthopaedic surgical instrument of claim 1, wherein the first body further includes a threaded aperture located on a superior side of the first main body.

9. The orthopaedic surgical instrument of claim 8, wherein the first main body includes a boss extending superiorly from the superior side and wherein the boss includes the threaded aperture located on the superior side of the first main body.

10. An orthopaedic surgical instrument system comprising:
- an orthopaedic broach including a tapered body extending distally from a proximal end to a distal end, the tapered body having a plurality of cutting teeth defined therein; and
- an orthopaedic broach extraction tool including:
    (i) a first body having a first main body and a first jaw extending distally from the first main body, wherein the first main body includes an aperture and a boss extending superiorly from a superior side of the first main body, wherein the boss includes a threaded aperture located on the superior side of the first main body,
    (ii) a second body having a second main body and a second jaw extending distally from the second main body, wherein the second jaw confronts the first jaw and the second main body includes a threaded aperture, and
    (iii) an adjustment screw extending through the aperture of the first main body and engaged into the threaded aperture of the second main body to couple the first body and the second body, wherein the adjustment screw is operable to cause the second jaw to move a first distance away from the first jaw that allows the orthopaedic broach to be positioned between the first jaw and the second jaw and is operable to cause the second jaw to move toward the first jaw to cause the first jaw and the second jaw to engage the cutting teeth of the orthopaedic broach while the orthopaedic broach is positioned between the first jaw and the second jaw to secure the orthopaedic broach extraction tool to the orthopaedic broach.

11. The orthopaedic surgical instrument system of claim 10, wherein the first jaw comprises (i) a first arm extending distally from a first end to a second end, wherein the first end of the first arm is attached to the first main body, and (ii) a first claw located at the second end of the first arm, and
wherein the second jaw comprises (ii) a second arm extending distally from a first end to a second end, wherein the first end of the second arm is attached to second main body, and (ii) a second claw located at the second end of the second arm, wherein the first claw and the second claw confront each other.

12. The orthopaedic surgical instrument system of claim 11, wherein the first arm extends distally from the first main body at an angle toward the second arm and wherein the second arm extends distally from the second main body at an angle toward the first arm such that a distance between the first end of the first arm and the first end of the second arm is greater than a distance between the second end of the first arm and the second end of the second arm.

13. The orthopaedic surgical instrument system of claim 10, wherein the operation of the adjustment screw causes the second main body to translate along the adjustment screw toward the first main body.

14. The orthopaedic surgical instrument system of claim 13, wherein:
- the first main body includes a track, and
- the second main body includes a rail received in the track, wherein the rail slides along the track when the second main body translates along the adjustment screw toward the first main body.

15. The orthopaedic surgical instrument system of claim 10, wherein the adjustment screw comprises (i) an elongated screw body having a first end and a second end opposite the first end, wherein the first end includes a threaded portion received in the threaded aperture of the second main body and (ii) a handle attached to the second end of the elongated screw body, wherein the handle is operable to thread the elongated screw body into the threaded aperture of the second main body to cause the second main body to translate along the elongated screw body toward the first main body.

16. The orthopaedic surgical instrument system of claim 15, wherein the elongated screw body includes a ring having a diameter greater than a diameter of the threaded portion and wherein the ring is captured in the first main body to secure the adjustment screw to the first main body.

17. A method of performing an orthopaedic surgical procedure on a proximal end of a patient's femur, the method comprising:
- inserting an orthopaedic broach in a medullary canal of a patient's surgically prepared femur, wherein the orthopaedic broach includes a tapered body extending distally from a proximal end to a distal end, the tapered body having a plurality of cutting teeth defined therein;
- securing an orthopaedic broach extraction tool to the orthopaedic broach while the orthopaedic broach is inserted into the medullary canal of the patient's femur, wherein securing the orthopaedic broach extraction tool comprises operating an adjustment screw of the orthopaedic broach extraction tool to move a second jaw of the orthopaedic broach extraction tool toward a first jaw of the orthopaedic broach extraction tool to cause the first and second jaws to engage the cutting teeth of the orthopaedic broach to secure the orthopaedic broach extraction tool to the orthopaedic broach; and
- extracting the orthopaedic broach from the medullary canal of the patient's femur using the orthopaedic broach extraction tool.

18. The method of claim 17, wherein extracting the orthopaedic broach from the medullary canal of the patient's femur using the orthopaedic broach extraction tool comprises attaching a reverse impaction tool to the orthopaedic broach extraction tool and using the reverse impaction tool to extract the orthopaedic broach.

* * * * *